United States Patent [19]

Nakajima et al.

[11] 4,038,034
[45] July 26, 1977

[54] AIR-FUEL RATIO SENSING DEVICE FOR INTERNAL COMBUSTION ENGINE

[75] Inventors: Yasuo Nakajima, Yokosuka; Kenji Yoneda, Yokohama, both of Japan

[73] Assignee: Nissan Motor Co., Ltd., Yokohama, Japan

[21] Appl. No.: 674,673

[22] Filed: Apr. 7, 1976

[30] Foreign Application Priority Data

Apr. 8, 1975 Japan .................................. 50-42627

[51] Int. Cl.² ...................... F16K 17/38; G01N 27/00; G05D 23/02
[52] U.S. Cl. .................. 23/255 E; 23/254 E; 137/468; 236/93 R; 236/101 E
[58] Field of Search ............ 23/232 E, 232 R, 254 E, 23/254 R, 255 E, 255 R; 236/15 E, 93 R, 101 E; 73/23, 116; 137/468

[56] References Cited

U.S. PATENT DOCUMENTS

| | | | |
|---|---|---|---|
| 2,698,022 | 12/1954 | Fahnoe | 137/468 X |
| 3,167,400 | 1/1965 | Fisher | 23/288 FA |
| 3,263,742 | 8/1966 | Rubin | 236/93 R |
| 3,846,080 | 11/1974 | MacLean et al. | 73/349 X |
| 3,936,794 | 2/1976 | Beaudoin et al. | 73/23 |

*Primary Examiner*—Joseph Scovronek
*Attorney, Agent, or Firm*—Lowe, King, Price & Markva

[57] ABSTRACT

An air-fuel ratio sensing device for an air-fuel ratio control system of an internal combustion engine, which device includes a sensing element exposed to exhaust gases passing through an exhaust gas passageway. A housing surrounding the sensing element has a plurality of openings to admit the exhaust gases into the housing, and a plurality of temperature responsive valves associated with the openings, respectively, which are closed when the exhaust gases exceed an excessively high temperature to prevent the sensing element from being deteriorated due to excessively high temperature of the exhaust gases.

4 Claims, 4 Drawing Figures

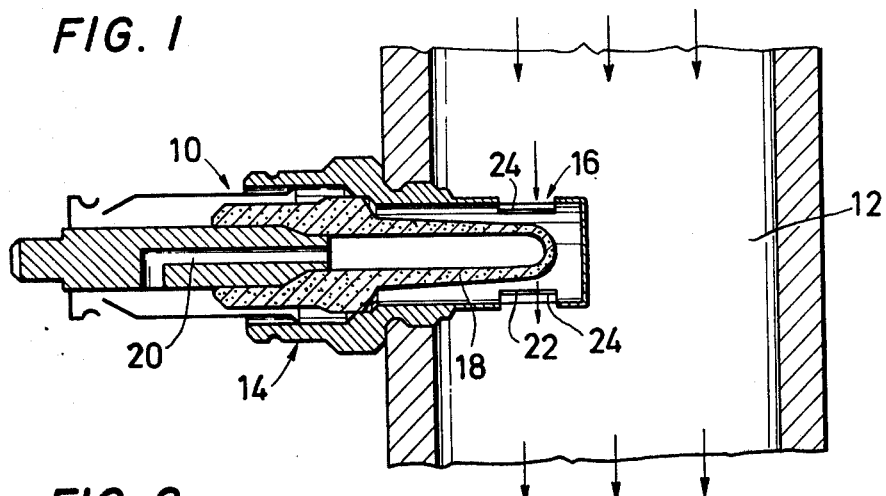
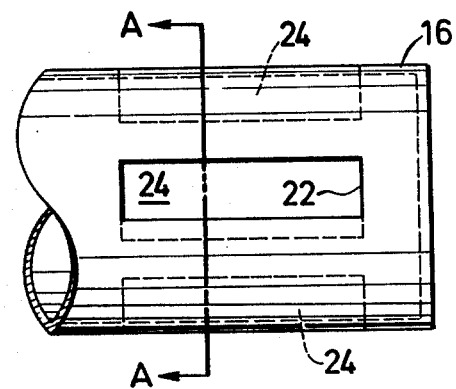
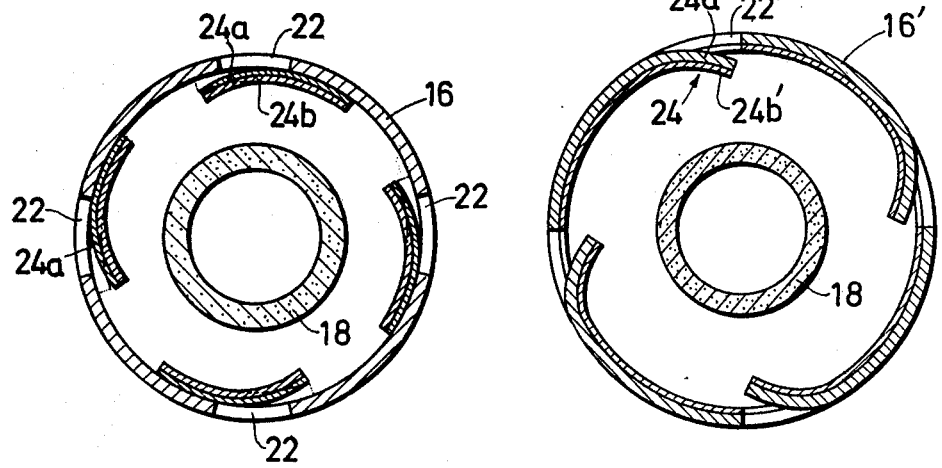

AIR-FUEL RATIO SENSING DEVICE FOR INTERNAL COMBUSTION ENGINE

This invention relates to an air fuel mixture control system for an internal combustion engine, and more particularly to an air-fuel ratio sensing device for such a control system.

As is well known in the art, it has been proposed to have an internal combustion engine equipped with a control system adapted to accurately control the air-fuel ratio of an air-fuel mixture supplied to the engine. The control system includes an air-fuel ratio sensing device such as an oxygen sensor or carbon monoxide sensor mounted in an exhaust system of the engine to detect the concentration of particular components contained in engine exhaust gases thereby producing a voltage signal in dependence thereon. This voltage signal is applied to the air-fuel ratio control system by which the air-fuel ratio of the air-fuel mixture supplied to the engine is controlled an optimum level.

The air-fuel ratio sensing device provides an accurate output signal at a relatively high temperature of, for instance, 400° to 800° C. If, however, the air-fuel ratio sensing device is exposed to extremely high temperature gases during high speed operation or under heavy load of the engine, it is deteriorated in performance efficiency and, in extreme cases, it is damaged. For this reason, it has been a usual practice to place the air-fuel ratio sensing device in a position away from the upstream side of the exhaust system. In this case, the sensing device is less responsive to the concentration of the particular components of the exhaust gases during idling or low speed operation of the engine resulting in a reduced reliability in the operation of the air-fuel ratio control system.

It is, therefore, an object of the present invention to provide an improved air-fuel ratio sensing device for an air-fuel ratio control system of an iternal combustion engine.

It is another object of the present invention to provide an improved air-fuel ratio sensing device which is highly reliable in operation over a wide range of temperature variations in engine exhaust gases.

It is another object of the present invention to provide an improved air-fuel ratio sensing device which is simple in construction and easy to manufacture.

It is still another object of the present invention to provide an improved air-fuel ratio sensing device including temperature control means for maintaining a sensing element of the device at an optimum temperature throughout varying operating conditions of the engine.

It is still another object of the present invention to provide an improved air-fuel ratio snsing device for an air-fuel ratio control system of an internal combustion engine, which device can be mounted at any desired position in an exhaust system of the engine and provide an accurate control signal throughout varying operating conditions of the engine.

It is a further object of the present invention to provide an improved air-fuel ratio sensing device for an air-fuel ratio control system of an internal combustion engine, which device has a long life and frequent replacement of the same is not required.

These and other objects, features and advantages of the present invention will become more apparent from the following description when taken in conjunction with the accompanying drawings, in which:

FIG. 1 is a cross sectional view of a preferred embodiment of an air-fuel ratio sensing device according to the present invention;

FIG. 2 is an enlarged fragmentary view of a part of the device shown in FIG. 1;

FIG. 3 is a cross sectional view taken on line A-A of FIG. 2; and

FIG. 4 is similar to FIG. 3 but shows a part of another preferred embodiment of the present invention.

Referring now to FIG. 1, there is shown an air-fuel ratio sensing device 10 mounted on an exhaust passageway 12 leading from an internal combustion engine of the type including an air-fuel ratio control system (not shown). The sensing device 10 comprises a casing threaded to the wall of the exhaust passageway 12, and a housing 16 integrally formed with the casing 14 and projecting into the exhaust passageway 12. The casing 14 fixedly supports therein a sensing element 18 such as a small sintered zirconium dioxide tube doped with certain metal oxides and closed at one end. The inside and outside surfaces of the tube are coated with a thin layer of platinum. The sensing element 18 extends into the exhaust gases, whereas its inner part is connected to the free atmosphere through an air passage 20.

As best shown in FIGS. 2 and 3, the housing 16 is formed with a plurality of openings or elongated slots 22 at circumferentially spaced positions through which engine exhaust gases enter the housing 16. According to an essential feature of the present invention, a plurality of temperature responsive valves 24 are mounted on the housing 16 at the respective openings 22 and serves as means for controlling the opening degree of each elongated slot 22 in dependence on the temperature of the exhaust gases passing through the exhaust passageway 12.

The temperature responsive valve 24 may comprise a bimetallic plate formed of two dissimilar metals welded together, different coefficients of expansion of the metals causing the plate to bend or curl when the temperature changes. Indicated as 24a is a metal having a low coefficient of expansion, and 24b indicates a metal having a high coefficient of expansion. It is to be noted that the coefficients of expansion of the metals are so selected as to cause the plate 24 to bend in a direction to close the opening 22 when the temperature of the exhaust gases exceeds a predetermined value of, for example, 800° to 900° C.

With the arrangement mentioned above, when the temperature of the exhaust gases varies within a range in which the sensing element 18 is suitably responsive to the particular components of the exhaust gases, the temperature responsive valves 24 are opened as shown in FIG. 3, allowing the exhaust gases to enter the housing 16.

When however, the temperature of the exhaust gases exceeds an excessively high level during heavy load or high speed operating condition of the engine, the temperature responsive valves 24 are caused to bend in a direction to close the openings 22 due to the difference in the coefficients of expansion of the metals. Consequently, the temperature of the gases in the housing 22 is maintained to a relatively low level so that deterioration of the sensing element 18 due to excessively high temperature can be satisfactorily prevented.

Since, thus, the air-fuel ratio sensing device 10 of the present invention has a plurality of temperature responsive valves, it can be located at the upstream side of the exhaust passageway 12. The result is that the sensing device 10 can operate in a reliable way even during idling or light load condition of the engine and, therefore, an accurate control signal for the air-fuel ratio control system can be generated throughout various operating conditions of the engine.

FIG. 4 illustrates another preferred embodiment of the present invention. In this illustrated embodiment, the housing 16' is made of dissimilar metals 24a' and 24b' and has a plurality of openings or elongated slots 22' at circumferentially spaced positions. When the sensing element 18 is actuating at an appropriate temperature, the openings 22' of the housing 16' are opened. However, when the temperature of the exhaust gases exceeds a predetermined value, the temperature responsive valves 24' are closed to prevent the sensing element 18 from being damaged due to excessively high temperature gases. This illustrated embodiment will provide ease of manufacturing.

It will now be appreciated from the foregoing description that in accordance with the present invention the sensing element of an air-fuel ratio sensing device is prevented from being directly exposed to the excessively high temperature of engine exhaust gases whereby an accurate output voltage signal can be obtained for a long period and frequent replacement of the sensing element is not required. Another advantage is that the air-fuel ratio sensing device can be located at an upstream side of an exhaust passageway of an internal combustion engine and it reliably operates to provide an accurate output signal even during idling or light load conditions of the engine.

While the present invention has been shown and described with reference to particular embodiments, it should be noted that various other changes or modifications may be made without departing from the scope of the present invention.

What is claimed is:

1. An air-fuel ratio sensing device for an air-fuel ratio control system of an internal combustion engine, comprising:
   a sensing element extending into an exhaust gas passageway so as to be exposed to exhaust gases flowing therein;
   a housing disposed about the sensing element and arranged to project into the exhaust gas passageway, said housing having a plurality of openings formed at circumferentially spaced positions; and
   a plurality of bimetallic valves arranged to flex toward said plurality of openings as the temperature thereof rises, and to close said plurality of openings when said exhaust gases exceed a predetermined temperature.

2. An air-fuel ratio sensing device as claimed in claim 1, in which said plurality of bimetallic valves comprise a plurality of bimetallic strips, one end of each strip being attached to a peripheral surface of the housing and arranged to flex toward the openings for closure thereof as the temperature of said bimetallic strips rises.

3. An air-fuel ratio sensing device according to claim 1, in which each of said bimetallic valves is integrally formed with said housing.

4. An air-fuel ratio sensing device according to claim 1, wherein said bimetallic valves are formed of metals having coefficients of expansion that flex said valves at a predetermined temperature of at least 800° C.

* * * * *